(12) United States Patent
Mills et al.

(10) Patent No.: US 10,908,052 B2
(45) Date of Patent: Feb. 2, 2021

(54) VENTURI VACUUM DEVICE FOR BIOLOGICAL SAMPLE COLLECTIONS

(71) Applicants: DeEtta Mills, Homestead, FL (US); Julian Mendel, Miramar, FL (US)

(72) Inventors: DeEtta Mills, Homestead, FL (US); Julian Mendel, Miramar, FL (US)

(73) Assignee: The Florida International University Board of Trustees, Miami, FL (US)

( * ) Notice: Subject to any disclaimer, the term of this patent is extended or adjusted under 35 U.S.C. 154(b) by 849 days.

(21) Appl. No.: 15/007,501

(22) Filed: Jan. 27, 2016

(65) Prior Publication Data

US 2017/0212015 A1 Jul. 27, 2017

(51) Int. Cl.
| | |
|---|---|
| *G01N 1/14* | (2006.01) |
| *C12Q 1/6806* | (2018.01) |
| *C12N 15/10* | (2006.01) |
| *G01N 1/10* | (2006.01) |

(52) U.S. Cl.
CPC ............... *G01N 1/14* (2013.01); *C12N 15/10* (2013.01); *C12Q 1/6806* (2013.01); *G01N 2001/1031* (2013.01); *G01N 2001/1427* (2013.01)

(58) Field of Classification Search
CPC .......... A61B 5/15003; A61B 5/150099; A61B 5/150213; A61B 5/150229; A61B 5/150236; A61B 5/150244; A61B 5/150389; A61B 5/153; G01N 1/14; G01N 2001/1418; G01N 2001/1427; G01N 2001/1436; G01N 2001/1031; C12Q 1/6806

USPC .................................................. 600/576, 578
See application file for complete search history.

(56) References Cited

U.S. PATENT DOCUMENTS

| | | | | |
|---|---|---|---|---|
| 2,541,621 | A * | 2/1951 | Thompson | A61M 5/31 604/187 |
| 2,634,856 | A * | 4/1953 | Perkins | A61M 5/002 206/571 |
| 3,978,846 | A * | 9/1976 | Bailey | A61B 5/15003 600/575 |
| 4,417,861 | A * | 11/1983 | Tolbert | F04B 43/0072 137/269.5 |
| 4,549,554 | A * | 10/1985 | Markham | A61B 10/0283 600/566 |
| 4,958,622 | A * | 9/1990 | Selenke | A61B 10/0045 600/578 |
| 5,257,527 | A * | 11/1993 | Kingsbury | G01N 1/2273 73/23.41 |
| 5,612,218 | A * | 3/1997 | Busch | G01N 1/36 435/288.1 |
| 5,902,279 | A * | 5/1999 | Powles | A61B 10/0283 600/578 |
| 6,179,815 | B1 * | 1/2001 | Foote | A61F 2/958 604/181 |
| 6,500,129 | B1 * | 12/2002 | Mahurkar | A61M 5/322 128/919 |

(Continued)

*Primary Examiner* — Patrick Fernandes
(74) *Attorney, Agent, or Firm* — Saliwanchik, Lloyd & Eisenschenk

(57) ABSTRACT

Devices and methods for collecting trace amounts of samples are provided. A device can utilize a sterile syringe integrated with a venturi-type vacuum source for sample collection. The device can be used in a variety of applications for collecting specimens that are otherwise difficult to retrieve using conventional sample collecting techniques.

20 Claims, 5 Drawing Sheets

(56) References Cited

U.S. PATENT DOCUMENTS

| | | | | |
|---|---|---|---|---|
| 6,758,824 B1* | 7/2004 | Miller | .................. | A61B 10/025 |
| | | | | 600/566 |
| 7,418,880 B1* | 9/2008 | Smith | ...................... | G01N 1/14 |
| | | | | 604/264 |
| 2004/0162500 A1* | 8/2004 | Kline | ..................... | A61B 5/097 |
| | | | | 600/532 |
| 2006/0009713 A1* | 1/2006 | Flaherty | .............. | A61M 5/1407 |
| | | | | 600/576 |
| 2010/0047914 A1* | 2/2010 | Peyman | ............. | G01N 33/6863 |
| | | | | 436/86 |
| 2010/0256662 A1* | 10/2010 | Racenet | ................. | A61B 10/06 |
| | | | | 606/170 |
| 2011/0282197 A1* | 11/2011 | Martz | ................... | A61M 5/007 |
| | | | | 600/432 |
| 2015/0289856 A1* | 10/2015 | Saqi | ........................ | B01L 3/502 |
| | | | | 422/534 |
| 2017/0055966 A1* | 3/2017 | Vetter | ................. | A61B 10/0266 |
| 2017/0173257 A1* | 6/2017 | Sarna | ................. | A61B 10/0291 |
| 2017/0325843 A1* | 11/2017 | Finci | .................. | A61B 17/4241 |

* cited by examiner

US 10,908,052 B2

VENTURI VACUUM DEVICE FOR BIOLOGICAL SAMPLE COLLECTIONS

GOVERNMENT SUPPORT

The subject invention was made with partial government support under a research project supported by the Florida Department of Agriculture and Consumer Services under contract number 020731 and partially through a contract (Subcontract No. 09-097G-FIU-2) from West Virginia University. The government has certain rights in the invention.

BACKGROUND OF THE INVENTION

Traditional swabbing or tape lift techniques are used to collect trace amounts of biological samples, such as epithelial cells and pollen grains. However, further recovery of DNA from those samples is often low due to the collection matrices not releasing the cells/DNA or interfering with amplification of DNA downstream due to samples adhering to gum and/or glues from the tapes used for lifting. In addition, certain methods of collecting environmental samples are invasive and may damage the living organisms from where the samples are obtained.

BRIEF SUMMARY

The subject invention provides devices and methods for collecting trace amounts of samples such as, for example, biological, environmental, and/or chemical specimens. A device can utilize a sterile syringe integrated with a venturi-type vacuum source for sample collection. Advantageously, the devices provided herein can be used in a variety of applications for collecting specimens that are otherwise difficult to retrieve using conventional sample collecting techniques.

In one embodiment, a portable device for collecting a trace amount of a specimen can include: a syringe including a barrel and a plunger fitted inside the barrel, the plunger having a piston at one end thereof, and the barrel having a first opening and a second opening through an outer surface thereof; and a length of vacuum tubing detachably connecting the barrel to a vacuum source through the first opening. The vacuum source can be a venturi-type vacuum source. The device can further include a specimen-collecting tool detachably connected to a tip of the syringe opposite the plunger.

In another embodiment, a method of collecting a trace amount of a specimen can include: providing a device described herein adjacent to the specimen to be collected; generating suction pressure at an opening of the specimen-collecting tool by sealing the second opening of the barrel while the vacuum source is in operation; and drawing the specimen through the opening of the specimen-collecting tool and into the barrel.

In another embodiment, a kit for collecting a trace amount of a specimen can include: a sterile specimen-collecting tool, which can be a silicone suction cup fitted with a porous membrane (e.g., a polycarbonate filter or a cotton gauze pad), a hollow metallic needle, or a pipette tip fitted with a filter; a sterile syringe that includes a barrel having a first opening and a second opening through an outer surface thereof, a plunger fitted inside the barrel and having a piston at one end thereof, and a tip opposite the plunger and capable of detachably connecting to the sterile specimen-collecting tool; and a length of vacuum tubing capable of detachably connecting the barrel of the sterile syringe to a venturi-type vacuum source. The kit can also include the venturi-type vacuum source that can be connected to the vacuum tubing. The kit can further include a sterile liquid stored in a sterile container, and the sterile liquid can be, for example, a biological buffer or an alcohol.

DETAILED DESCRIPTION

The subject invention provides device and methods for collecting trace amounts of samples such as, for example, biological, environmental, and/or chemical specimens. A device can utilize a sterile syringe integrated with a venturi-type vacuum source for sample collection. Advantageously, the devices provided herein can be used in a variety of applications for collecting specimens that are otherwise difficult to retrieve using conventional sample collecting techniques.

Figure 1:
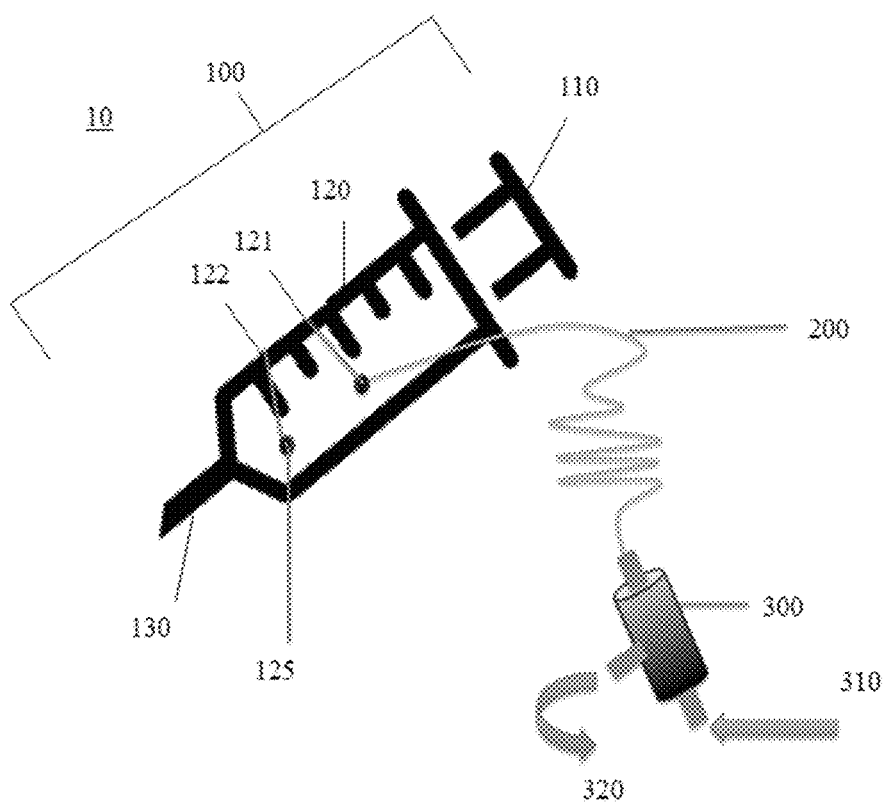
FIG. 1 shows a schematic view of a specimen-collecting device according to an embodiment of the subject invention.

FIG. 1 shows a schematic view of a device according to an embodiment of the subject invention. Referring to FIG. 1, a device 10 for collecting a trace amount of a specimen can include a syringe 100 and a length of vacuum tubing 200 connecting (e.g., detachably connecting) the syringe 100 to a vacuum source 300 (e.g., a venturi-type vacuum source).

The device can further include a specimen-collecting tool (not shown in FIG. 1) detachably coupled to the syringe 100 (e.g., to the tip 130 of the syringe 100). The syringe 100 can include a plunger 110 with a piston (e.g., a rubber piston) at one end, and the plunger 110 can be fitted inside a barrel 120, which can be transparent, of the syringe 100. The barrel 120 can have a first opening 121 and a second opening 122 on an outer surface thereof. One or both of the openings 121,122 can include a grommet 125 (e.g., a rubber grommet) around it. The length of vacuum tubing 200 can detachably connect the barrel 120 of the syringe to the vacuum source 300 (e.g., a venturi-type vacuum source) through one of the openings 121, 122 (e.g., the first opening 121). The length of tubing 200 can be a pre-selected or predetermined length of tubing.

The vacuum source 300 can be a venturi-type vacuum source, which can include an input of pressurized fluid 310

(e.g., compressed air such as compressed $CO_2$) and an outlet for lower-pressure fluid 320 (e.g., lower-pressure $CO_2$).

Figure 2:
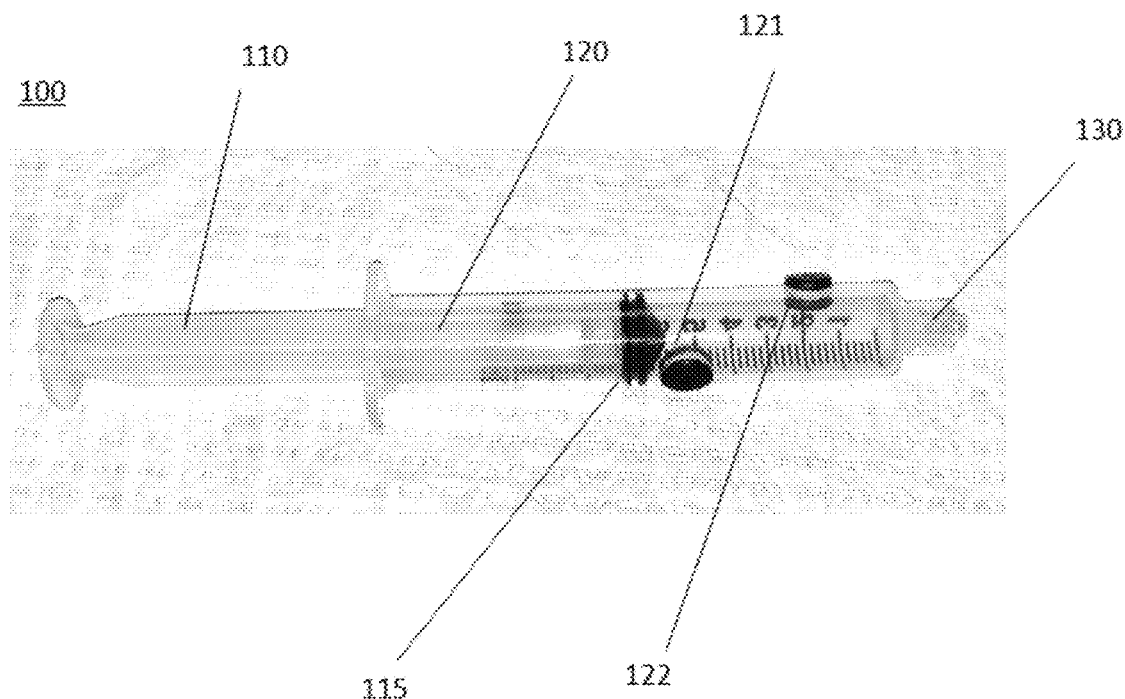
FIG. 2 shows an image of a syringe used in a collecting device according to an embodiment of the subject invention.

FIG. 2 shows an image of a syringe that can be used in a device of the subject invention. Referring to FIG. 2, the plunger 110, piston 115, barrel 120, tip 130, first hole 121, and second hole 122 can be seen. The barrel 120 shown in FIG. 2 is a transparent barrel with graduation markings, but embodiments of the subject invention are not limited thereto.

Figure 3A:
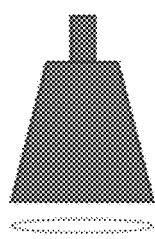
FIG. 3A shows a silicone suction cone as an exemplary specimen-collecting tool adapted with a polycarbonate filter.
Figure 3B:
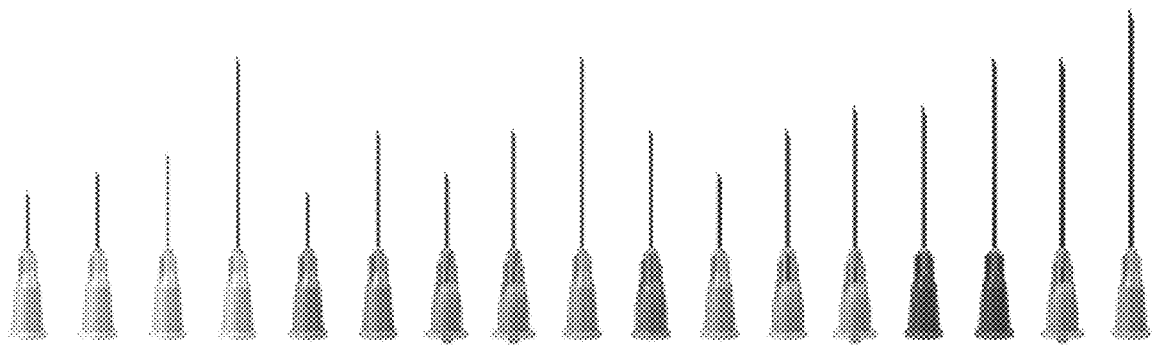
FIG. 3B shows hollow metallic needles in a variety of sizes that can be used as specimen-collecting tools to be attached to the tip of the sterile syringe.
Figure 3C:
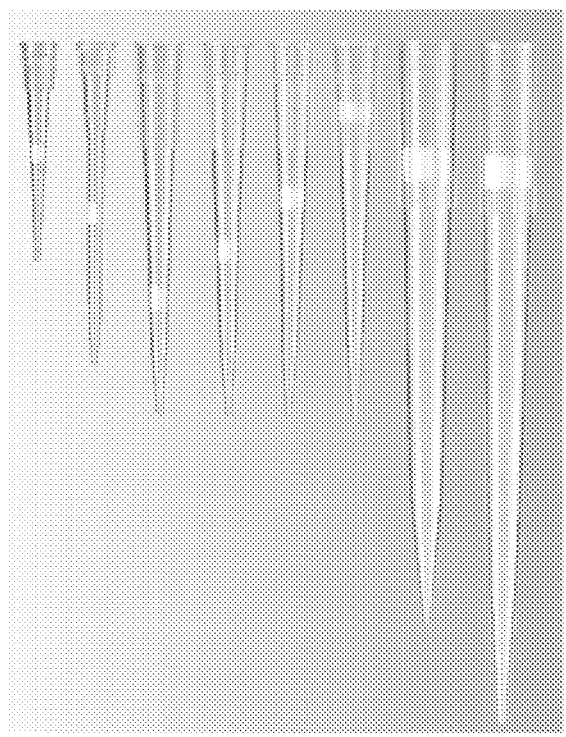
FIG. 3C shows pipette tips fitted with filters that can be used as specimen-collecting tools to be attached to the tip of the sterile syringe.

In certain embodiments, the specimen-collecting tool can be detachably coupled to the tip of the syringe and can be selected from silicone suction cups fitted with porous membranes filters (as depicted in FIG. 3A), hollow metallic needles (FIG. 3B), and pipette tips fitted with filters (FIG. 3C). The porous membranes can be, for example, polycarbonate sheets or cotton gauze pads, though embodiments are not limited thereto.

In accordance with some embodiments of the subject invention, the specimen of interest can be selected from human cellular materials, plant materials, volatile organic compounds (VOCs), particles, fibers, and microorganisms, in both dry and fluid forms. Non-limiting examples of specimens that can be collected using the device provided herein include human epithelial cells, single hairs, pollen grains, gunshot residue, and fungal spores residing inside plants.

In comparison with conventional swabs and tapes used to collect cellular materials containing DNA samples, exemplary embodiments of the device provided herein have the ability to collect samples with a silicone suction cup fitted with porous membranes, e.g., polycarbonate filters, without causing downstream interference, which is critical for trace evidence analyses. In addition, the recovery efficiency from polycarbonate filters is expected to be significantly higher than those used in related art methods due to its low affinity for DNA and other cellular materials.

In some embodiments, the device can be used to collect VOCs using a silicone suction cup fitted with a cotton gauze pad. Embodiments of the subject invention can also be used to analyze scents collected directly from an individual or indirectly from a surface touched by the individual.

In certain embodiments, the specimen can also be collected from porous surfaces including, but not limited to, fabrics and wood.

In some embodiments, the device provided herein can be used to collect environmental samples from other living organisms in a non-invasive manner. As a non-limiting example, when the syringe is fitted with a hollow metallic needle as the specimen collecting tool, microbial communities can be directly collected from inside a tree by inserting the needle into the tree, leaving behind only a small hole. Alternatively, the needle can be inserted through holes already existing on the tree. This technique can prevent or inhibit physical damage to the tree and exposure to pests such as, for example, invasive beetles that can spread fungal phytopathogens across forests and commercial tree groves.

Advantageously, with appropriate collecting tools attached to the syringe, samples from difficult-to-reach locations and/or found in other living organisms can be readily retrieved without potentially damaging the host organisms.

In some embodiments, a dry specimen can be dissolved or suspended in a liquid before being collected. The liquid provided herein can be, for example, a biological buffer or ethanol, though embodiments are not limited thereto. Optionally, chemicals used to preserve the specimen can also be added to the liquid. The nature and the amount of the liquid used can be readily determined by those skilled in the art according to the nature of the specimen of interest. This technique can be necessary for collecting cellular and DNA materials left behind in a touch sample or for collecting a trace sample from a porous surface.

In order to accommodate the wide array of specimens that can be collected using the devices provided herein, the pore size of a membrane filter can be determined by those skilled in the art based on the nature of the specimen of interest. In cases where porous membranes are used as filters, further analyses of the specimen, including, but not limited to, DNA extraction, VOC separation, culturing, and metabolomics study, can be conducted by processing the filters with the specimen intact. In certain embodiments, a specimen can be isolated from the filters by using an art-recognized extraction method.

In some embodiments, both the syringe and the collecting tool provided herein are sterile and preferably disposable in order to eliminate possible cross-contamination typical of related art collection techniques using non-sterile, fiber-based sample collecting matrices such as, for example, cotton swabs. In the cases where a buffer is used to dissolve or suspend the specimen, the barrel of the syringe can be optionally rinsed with the buffer prior to sample collection in order to prevent or inhibit contamination.

In some embodiments, the venturi-type vacuum source can be powered by a compressed fluid medium (e.g., 310 in FIG. 1 shows the compressed fluid entering the vacuum source 300). In further embodiments, the fluid medium can be a gaseous species such as, as non-limiting examples, compressed carbon dioxide and/or compressed air.

In one embodiment, the venturi-type vacuum source can include a compressed gas tank in connection with a nozzle, which then widens into a venturi diffuser, and a vacuum port located between the nozzle and the diffuser. Based on the principles of the venturi effect, vacuum is created in the space between the nozzle and the diffuser when the compressed gas enters the constricting nozzle and then increases in velocity as it flows into the diffuser. The vacuum port is fitted with a one-way check valve in order to prevent passage of the liquid specimen flowing back into the vacuum source.

In an embodiment, one end of the vacuum tubing can be connected to the vacuum port while the other end can be detachably connected to one of the openings (e.g., the first opening) located on the outer surface of the barrel of the syringe. In a further embodiment, the length of the vacuum tubing and the size of the compressed gas tank can be selected to maximize the portability of the overall collection device and the kit provided herein. Advantageously, the venturi-type vacuum source does not require electric power, enhancing its portability and ease of operation.

As used herein, "detachably connected" requires that the parts be easily released or detached by a user without the use of tools. For example, the parts can be pliable interfering plastic parts, or can use friction grip or the like, and can be releasable or detachable by simple application of force via the operator's hand. In an exemplary embodiment, the vacuum tubing is connected to the first opening of the barrel via a rubber grommet (125 in FIG. 1) to prevent leakage of the specimen and/or the loss of vacuum.

Specimen collection can be accomplished when the opening that does not have the vacuum tubing connected thereto (e.g., the second opening) on the barrel is temporarily sealed, thus creating a pressure difference around the opening of the collecting tool, which then forces the specimen into the barrel of the syringe, the specimen optionally passing through a porous membrane filter before entering the barrel. This can be accomplished by, for example, a user covering the opening with his or her finger. The opening should be covered to create a complete seal around the opening.

In certain embodiments, the two openings on the body of the barrel are optionally sealable when the collecting device is not in operation. A variety of pliable parts can be used for sealing including, but not limited to, stoppers (e.g., rubber stoppers) and grommets (e.g., rubber grommets).

In an embodiment, a method of collecting a trace amount of a specimen can include providing a specimen collecting device as provided herein, generating suction pressure at the opening of the specimen-collecting tool by sealing the opening that is located on the barrel and does not have the vacuum tubing coupled thereto (e.g., the second opening) while the vacuum source (e.g., venturi-type vacuum source) is in operation, and drawing the specimen through the opening of the collecting tool into the barrel. The method can further include releasing the seal of the second opening.

In certain embodiments, the opening that does not have the vacuum tubing coupled thereto (e.g., the second opening) can be sealed with an operator's finger during specimen collection. Alternatively, the opening can be sealed with the pliable parts provided herein.

In an embodiment, the method optionally includes delivering an appropriate amount of a liquid to the specimen using the same syringe with which the specimen is subsequently collected, the syringe being disconnected from the vacuum source and the two openings being optionally sealed during this step. In a further embodiment, the liquid can dissolve or suspend the specimen, helping to preserve and/or extract the specimen that is otherwise difficult to collect due to its nature and location. The nature and the amount of the liquid delivered to the specimen are determined by those skilled in the art in accordance with the nature of the specimen to be collected.

Alternatively, the liquid can be delivered to the specimen prior to collection using a number of suitable storage containers, provided that the containers are sterile and preferably disposable in order to avoid cross-contamination. The choice of storage container used for applying the liquid provided herein can be readily determined by those skilled in the art in accordance with the nature and the amount of liquid of interest.

In an embodiment, the liquid can be a biological buffer solution, which optionally includes chemicals capable of preserving cellular materials, e.g., DNA, present in the specimen.

In an embodiment, buffer solution can be injected to a site where microorganisms are present for collection, followed by drawing the microorganisms into the vacuum-operated device that is fitted with a membrane filter, e.g., a polycarbonate filter. In a further embodiment, this procedure can be repeated to maximize the amount of specimen collected.

In an embodiment, buffer solution can be applied to dried specimen present on and/or embedded in porous surfaces, such that by dissolving the specimen those skilled in the art can then utilize the vacuum-powered device provided herein to complete the collection.

In a further embodiment, the method can include, instead of releasing the seal of the second opening, shutting off the vacuum source following the collection of the specimen.

In another embodiment, a portable specimen collecting kit can include a venturi-type vacuum-powered device as provided herein and at least one type of specimen-collecting tool with at least one type of porous membrane filter for collecting a variety of specimens, wherein both the collecting tool and the membrane filter are sterile. In an embodiment, the kit can include an acceptable liquid stored in a sterile, preferably disposable, container. The kit can further include a syringe as described herein, and the syringe can be sterile.

Advantageously, without needing electric power to operate, the portable specimen collecting kit enables the sterile collection of a trace amount of dry and/or wet specimens from hard-to-retrieve locations in a non-invasive manner.

EXAMPLES

The following are examples that illustrate the aforementioned embodiments and should not be construed as limiting. All of the chemical supplies provided herein, unless otherwise noted, were obtained via commercial sources and are readily available for procurement.

Example 1

The device shown in FIG. 1 was evaluated for collecting human touch samples as well as mock touch samples. Mock touch samples were generated using a known number of epithelial cells pipetted directly onto 6" sterile stainless steel bars and allowing them to dry under a fume hood. These cells were used in a comparison study between the vacuum-powered collection method and related art cell collection method using cotton swabs. The vacuum source was a venturi-type vacuum source with a compressed $CO_2$ gas inlet (310 in FIG. 1) and a lower-pressure $CO_2$ gas outlet (320 in FIG. 1). Each of the holes 121, 122 included a rubber grommet 125, and the second hole 122 was sealed with a user's finger to create the vacuum in the syringe during sample collection.

The vacuum-powered collecting device utilizing a venturi system to generate suction was connected to a gauged tank of compressed air. For each sampling event, a polycarbonate (PC) filter with a pore size of approximately 1.2 μm (Millipore Inc. Billerica, Mass.) was cut to a diameter of approximately 12 mm to fit inside a silicone suction cup, which was then attached to the sterile syringe. The filter was affixed to the cup under suction and placed in direct contact with the sampling area on the stainless steel bars, followed the wiping of the surface of the stainless steel bars. Where cells were pipetted onto the bars and allowed to dry, the surface of the bars was moistened with 1×PBS immediately before vacuum collection. After sample collection, the filters were removed and placed into 2 mL tubes for DNA extraction. To ensure no exogenous DNA was present on the polycarbonate filters prior to the collection, blank filters were tested and the results showed no DNA present due to manufacturing and/or handling practices.

Results displayed in Table 1 show the average DNA yield collected from mock samples using two different collection methods. The venturi-vacuum device produced more reproducible results than cotton swabs. A large portion of cells captured by the cotton swabs can be retained in the fibers and are thus unavailable for analysis. For the sample size on the order of approximately 50 cells, the venturi-vacuum device shows advantage in collecting more DNA than using cotton swabs.

TABLE 1

The average DNA yield from a known number of cells spotted directly onto the stainless steel bars, i.e., the mock samples, and recovered using cotton swabs and a venturi-vacuum device fitted with polycarbonate filters, respectively. (N = 3)

|  | 5000 cells Avg DNA yield (ng ± SE) | 500 cells Avg DNA yield (ng ± SE) | 50 cells Avg DNA yield (ng ± SE) |
| --- | --- | --- | --- |
| Vacuum | 5.574 ± 0.201 | 0.168 ± 0.016 | 0.043 ± 0.014 |
| Swab | 5.408 ± 3.895 | 1.994 ± 1.788 | 0.038 ± 0.010 |

In addition to the mock touch samples, actual touch samples were collected from human subjects. Subjects were required to refrain from washing their hands for a minimum of three hours prior to the sampling. Three individuals were presented with sterilized stainless steel bars and asked to grasp them with their dominant hand for two minutes, optionally rolling the bar within their hands. The stainless steel bars were then sterilized by cleaning with 95% ethanol and wiping with DNA Away™ (Thermo Fisher Scientific, Waltham, Mass.), followed by autoclaving. As a control, the sterilized steel bars were tested for DNA prior to experiments and the results were negative for the presence of DNA, as expected.

Figure 4:
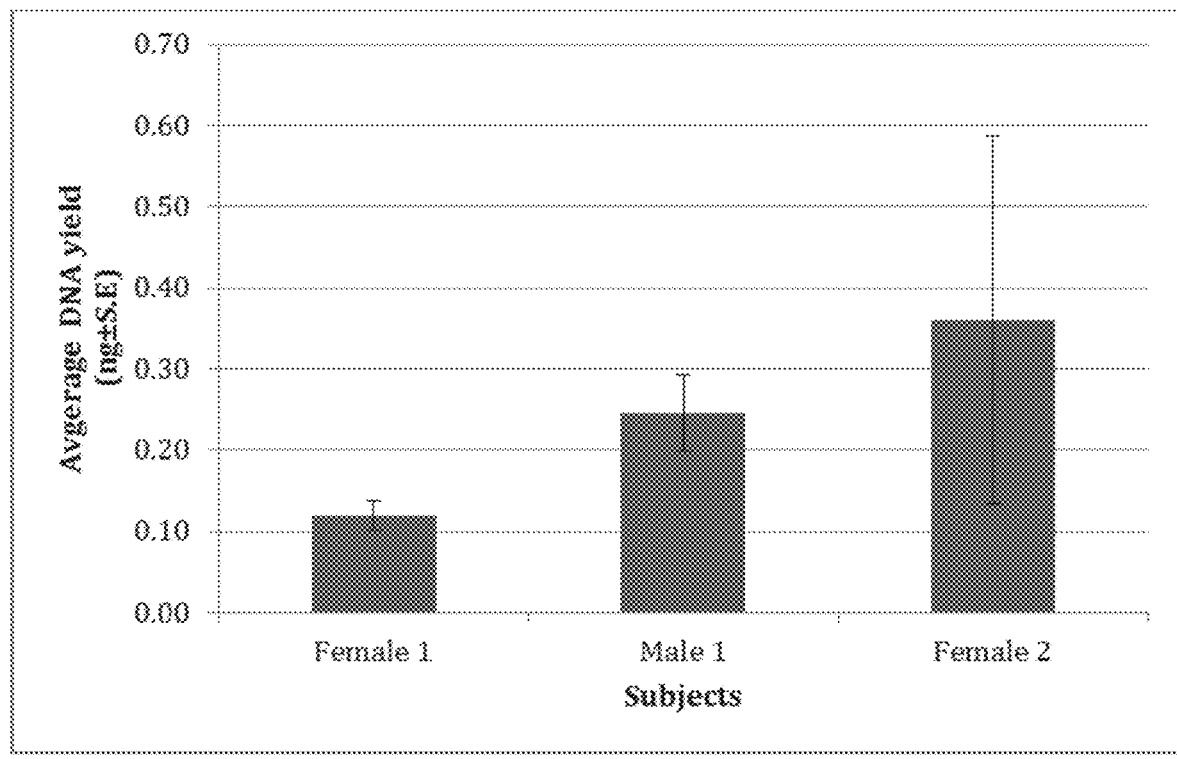
FIG. 4 shows the average DNA yields from three subjects' touch samples (N=3) on stainless steel bars collected using a venturi-vacuum device in accordance with an embodiment of the invention and processed using Quantiplex qPCR chemistries.

As shown in FIG. 4, the venturi-vacuum device successfully collects cells deposited by individuals touching objects, where N=3. The average DNA recovered from these samples would be sufficient to obtain useful DNA profiles. The high variability in DNA recovered from individuals over a 3-day period speaks to the variability in shedding that can be observed within each individual.

In a further experiment, the venturi-vacuum device provided herein was used to collect touch samples from 100 individuals, the results of which are shown in Table 2. The large standard deviations were indicative of the large variability of deposited cells and DNA yield from 100 individuals. The average DNA yield of approximately 2.16 ng is greater than the required amount for full forensic profile analysis.

TABLE 2

The average DNA yield (ng/µL) from 100 individual touch samples using a Quantiplex kit and mtDNA copy number yields. The average DNA yield for 100 subjects was approximately 2.0 ng with a range of 0.008-35 ng.

| Number of samples | Average Conc. (ng/µL) | SD | Average Total yield (ng) | SD |
| --- | --- | --- | --- | --- |
| 100 | 0.086 | ±0.20 | 2.16 | ±4.94 |

| Number of Samples | Average copy number/µL | SD | Average yield (total copy number) | SD |
| --- | --- | --- | --- | --- |
| 100 | $7.27 \times 10^3$ | $±1.60 \times 10^4$ | $1.82 \times 10^5$ | $±4.02 \times 10^5$ |

In summary, the data presented herein indicate that the venturi-vacuum device fitted with polycarbonate filters as a collection tool is an advantageous alternative to related art methods involving cotton swabs, and can produce sufficient and reproducible yields of DNA from human touch samples.

Example 2

The venturi-vacuum device used in Example 1 was applied to the collection of fungal spores from avocado trees infected with *Raffaelea lauricola*, which were introduced by beetles boring within the avocado trees. The outer bark of avocado trees infected with a fungal pathogen was removed using a hatchet to reveal the inner xylem sapwood where the fungus thrived. A 1×PBS was used to flush beetle canals and the sapwood to dislodge fungal spores. The vacuum device fitted with PC filters was used to collect spores. In order to determine whether spores were collected, the filters were shredded and placed onto malt extract agar plates and monitored for fungal growth.

Figure 5:
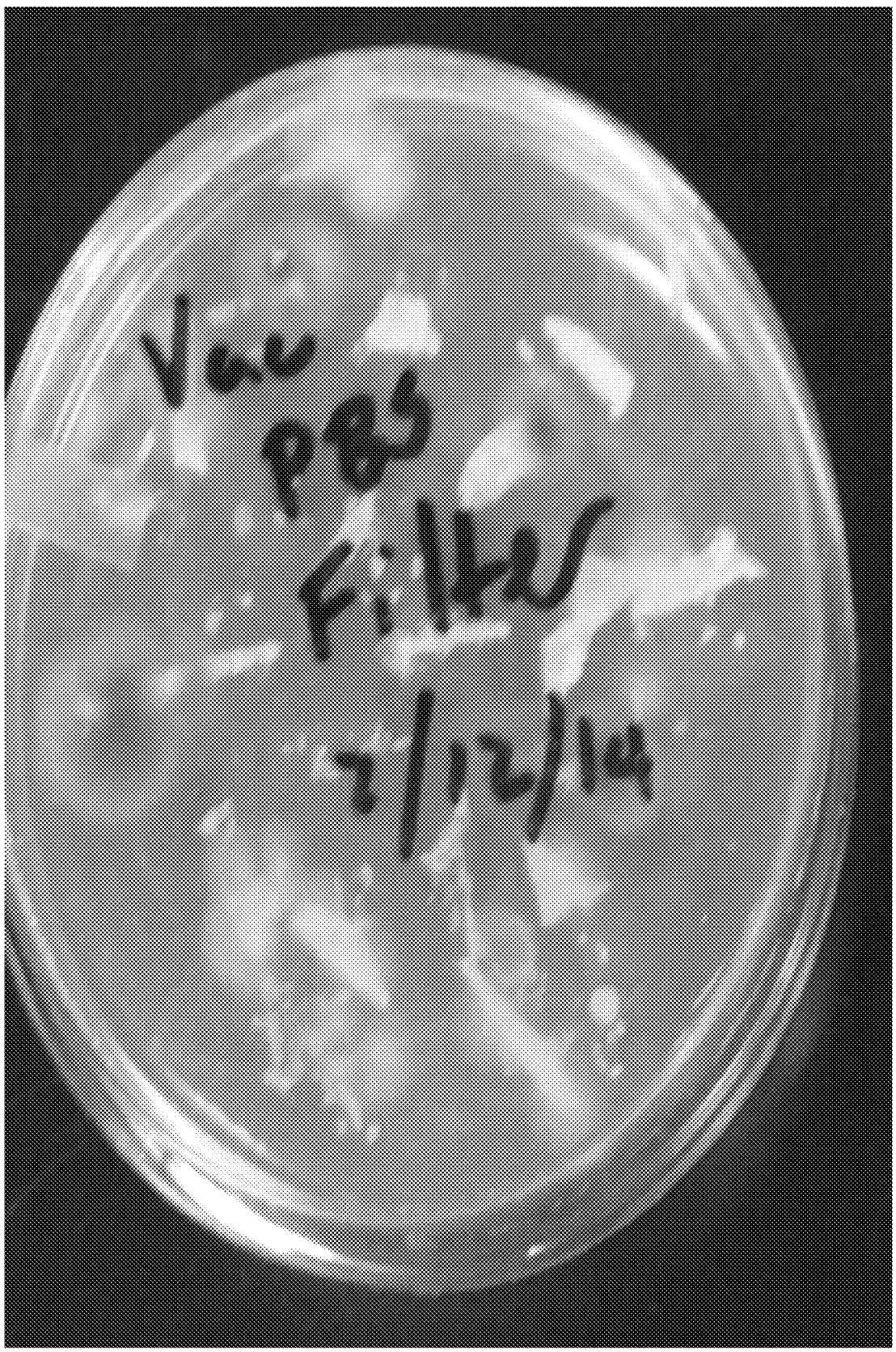
FIG. 5 is a photograph showing fungal growth from polycarbonate filters used in sample collection on avocado trees.

As shown in FIG. 5, fungal growth was observed on malt extract plates, indicating that fungal spores were successfully collected using the vacuum device. This application can be proven useful in the diagnosis of various plant pathogens that are not easily identifiable by other related methods.

Example 3

Pollen grains found on clothing were collected using the device used in Example 1, including a PC filter. A known number of pollen grains were placed onto a piece of a garment with some of the grains being embedded into the fabric. The sample area was then vacuumed using the device, which collected the pollen sample onto the PC filter. The filters were then observed under the microscope and the number of grains recovered was subsequently calculated. Again, the results indicated successful collection.

Example 4

Figure 6:
FIG. 6 is a photograph of a polycarbonate filter used in a venturi-vacuum device after pollen recovery trial, in which 11 pollen grains were recovered out of 16.

Pollen grains found on objects were collected using the device used in Example 1, including a PC filter. A suspension of pollen grains in 1×PBS was created, and 500 µL of the suspension was pipetted onto stainless steel bars and the number of pollen grains present was counted under a microscope. The vacuum device was then applied and the number of pollen grains collected on the filter was determined through microscopic images of the PC filter, as shown, for example, in FIG. 6.

Example 5

Non-invasive sampling of microbial communities from inside a tree was conducted using the device used in Example 1. The device was used to collect fungal phytopathogens spread by invasive beetles residing inside the tree. A small amount of buffer was first injected to beetle galleries using the sterile syringe, followed by quickly applying the vacuum to flush out the samples. The procedure was repeated several times in order to maximize the amount of fungal samples collected onto the PC filters. The filters were processed for metabolomics analyses, DNA extractions, and culturing without having damaged the tree. The results indicated successful collection.

The examples and embodiments described herein are for illustrative purposes only and various modifications or changes in light thereof will be suggested to persons skilled in the art and are included within the spirit and purview of this application. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

All patents, patent applications, provisional applications, and publications referred to or cited herein (including those in the "References" section, if present) are incorporated by reference in their entirety, including all figures and tables, to the extent they are not inconsistent with the explicit teachings of this specification.

What is claimed is:

1. A portable device for collecting a trace amount of a specimen, the device comprising:
   a syringe comprising a cylindrical barrel having a side surface, a tip having a tip opening, and a plunger fitted inside the barrel opposite the tip, the plunger having a piston at one end thereof; and
   a length of vacuum tubing,
   the cylindrical barrel comprising: a first opening through the side surface thereof; and a second opening through the side surface thereof,
   the length of vacuum tubing detachably coupling the cylindrical barrel to a vacuum source through the first opening by connecting directly to an inside of the cylindrical barrel, and
   the second opening being open to the environment.

2. The device according to claim 1, the vacuum source being a venturi-type vacuum source.

3. The device according to claim 1, further comprising a specimen-collecting tool detachably connected to the tip of the syringe.

4. The device according to claim 3, the specimen-collecting tool being sterile.

5. The device according to claim 1, the syringe being sterile.

6. The device according to claim 2, the venturi-type vacuum source being powered by compressed gas.

7. The device according to claim 3, the specimen-collecting tool being selected from the group consisting of: a silicone suction cup fitted with a porous membrane; a hollow metallic needle; and a pipette tip fitted with a filter.

8. The device according to claim 3, the specimen-collecting tool being a silicone suction cup fitted with a porous membrane, and
   the porous membrane being selected from the group consisting of: a polycarbonate sheet; and
   a cotton gauze pad.

9. The device according to claim 1, the syringe being configured such that when the second opening is temporarily sealed, a pressure difference is created around the tip opening such that the specimen can be collected into the cylindrical barrel.

10. The device according to claim 1, the first opening comprising a rubber grommet configured to receive the length of vacuum tubing.

11. A method of collecting a trace amount of a specimen, the method comprising:
    providing the device according to claim 3 adjacent to the specimen to be collected;
    generating suction pressure at an opening of the specimen-collecting tool by sealing the second opening of the cylindrical barrel while the vacuum source is in operation; and
    drawing the specimen through the opening of the specimen-collecting tool and into the cylindrical barrel.

12. The method according to claim 11, the vacuum source being a venturi-type vacuum source.

13. The method according to claim 11, further comprising releasing the seal of the second opening.

14. The method according to claim 11, the syringe being sterile, and the specimen-collecting tool being sterile.

15. The method according to claim 12, the step of generating suction pressure at an opening of the specimen-collecting tool by sealing the second opening of the cylindrical barrel while the venturi-type vacuum source is in operation comprising sealing the second opening of the barrel with a finger of a user of the device.

16. The method according to claim 11, the specimen-collecting tool being a silicone suction cup fitted with a porous membrane, and
    the porous membrane being selected from the group consisting of: a polycarbonate sheet; and
    a cotton gauze pad.

17. A kit for collecting a trace amount of a specimen, the kit comprising:
    a sterile specimen-collecting tool selected from the group consisting of: a silicone suction cup fitted with a porous membrane that is a polycarbonate filter or a cotton gauze pad; a hollow metallic needle; and a pipette tip fitted with a filter;
    a sterile syringe, the sterile syringe comprising:
        a tip configured to detachably connect to the sterile specimen-collecting tool, the tip comprising a tip opening;
        a cylindrical barrel having a first opening and a second opening, both the first opening and the second opening being through a side surface of the cylindrical barrel; and
        a plunger fitted inside the cylindrical barrel opposite the tip, the plunger having a piston at one end thereof; and
    a length of vacuum tubing configured to couple the cylindrical barrel of the sterile syringe to a venturi-type vacuum source by coupling to the first opening and connecting directly to an inside of the cylindrical barrel,
    the second opening being open to the environment.

18. The kit according to claim 17, further comprising the venturi-type vacuum source, and a sterile liquid stored in a sterile container, the sterile liquid being selected from the group consisting of: a biological buffer; and an alcohol.

19. The kit according to claim 17, the sterile syringe being configured such that when the second opening is temporarily sealed, a pressure difference is created around the tip opening such that the specimen can be collected into the cylindrical barrel.

20. The kit according to claim 17, the first opening comprising a rubber grommet configured to receive the length of vacuum tubing.

* * * * *